US005522792A

United States Patent [19]
Bassett et al.

[11] Patent Number: 5,522,792
[45] Date of Patent: Jun. 4, 1996

[54] HIP POSITIONING APPARATUS

[75] Inventors: C. Andrew L. Bassett, Bronxville, N.Y.; Govert L. Bassett, Raleigh, N.C.

[73] Assignee: Osteodyne, Inc., Morrisville, N.C.

[21] Appl. No.: 291,474

[22] Filed: Aug. 17, 1994

[51] Int. Cl.[6] .................................................. A61F 5/00
[52] U.S. Cl. ........................... 602/19; 602/24; 5/601
[58] Field of Search ............................ 602/19, 23, 24, 602/25; 128/846, 892; 5/600, 601, 612, 602; 428/100, 112, 136, 185, 907

[56] References Cited

U.S. PATENT DOCUMENTS

| | | | |
|---|---|---|---|
| 2,020,399 | 11/1935 | Culver et al. | 602/19 |
| 2,492,920 | 12/1949 | Koster | 602/24 |
| 3,509,876 | 5/1970 | Pilz | 5/601 |
| 3,759,252 | 9/1973 | Berman | 602/19 |
| 3,766,384 | 10/1973 | Anderson | 5/601 |
| 4,249,523 | 2/1981 | Bidwell | 602/24 |
| 4,433,678 | 2/1984 | Spann | 602/24 |
| 4,434,792 | 3/1984 | Rosenberg | 602/24 |
| 4,481,940 | 11/1984 | Kurtz et al. | 602/24 |
| 4,495,943 | 1/1985 | Kurtz et al. | 602/24 |
| 4,520,803 | 6/1985 | Quest | 602/24 |
| 4,520,805 | 6/1985 | St. Vincent et al. | 602/24 |
| 4,543,948 | 1/1985 | Phillips et al. | 602/24 X |
| 4,681,308 | 7/1987 | Rice | 5/601 |
| 4,872,656 | 10/1989 | Brendgord et al. | 5/601 |
| 5,147,286 | 9/1992 | Meals | 602/24 |
| 5,277,681 | 1/1994 | Holt | 482/112 |
| 5,362,305 | 11/1994 | Varn | 602/24 |

*Primary Examiner*—Richard J. Apley
*Assistant Examiner*—Kim M. Lee
*Attorney, Agent, or Firm*—Finnegan, Henderson, Farabow, Garrett & Dunner

[57] ABSTRACT

A hip positioning apparatus for maintaining an individual in an immobilized position for Dual X-ray Absorptiometry (DXA). A patient positions his or her groin against a centering member mounted on a frame. A pair of knee restraints mounted to the frame secures the knees of the individual in a manner to ensure that the knees are fully extended and the legs of the individual are spaced apart a predetermined amount. A pair of foot restraints pivotally mounted to the frame holds the individual's groin against the centering member and immobilizes the legs of the individual relative to the frame, Each of the foot restraints holds the respective one of the individual's feet at a predetermined angle relative to the individual's body.

14 Claims, 5 Drawing Sheets

HIP POSITIONING APPARATUS

BACKGROUND OF THE INVENTION

1. Field of the Invention

The present invention relates to the field of hip positioning, especially for analyzing risk of fracture, evaluating bone gain or loss, and effect of fracture treatment. More specifically, this invention relates to hip positioning of individuals prior to using Dual X-ray Absorptiometry (DXA).

2. Description of the Related Art

Bone loss almost always follows menopause. As individuals age, they lose bone substance and become increasingly susceptible to fractures. Elderly individuals suffer an increased incidence of broken bones, particularly in the wrist, shoulder, spine, and hip. Of these breaks, hip fractures are often the most serious to the patient as well as to society.

A hip fracture in an elderly individual usually requires an operation to stabilize the break and improve the prognosis. Even after an operation, up to 20% of fracture patients still die, while the remainder often require chronic hospital or nursing home care. It costs an estimated ten billion dollars annually to care for those with broken hips caused by loss of bone or osteoporosis. As our elderly population continues to grow, the financial drain will increase each year.

Current technology allows doctors to predict the risk of hip fracture by determining the amount of bone remaining in the specific area of the proximal femur. Most doctors use DXA scanning to measure a bone mineral density (BMD) and bone mineral concentration (BMC) of several areas of the hip. Usually, a patient lies on a scanning table with only the patient's foot fixed to a positioning device. The positioning device provides support for adducting the patient's foot 20 degrees. Adduction refers to rotating an individual's limb inward toward the median axis of the body, and abduction refers to rotating an individual's limb outward from the median axis of the body.

Current devices do not attempt to fix the position of the hip and knee in any particular location, however. This is unfortunate because the position of the hip, knee, and foot greatly affect the femoral neck's aspect to a DXA scanning beam. As a result, the BMD and BMC measurements often vary between scans. Successive hip scans of the same patient may vary by 3–4%, which is up to three times greater than a scanning machine's margin of error. Variations this large hamper doctors and researchers attempting to assess BMD gains or losses in the femoral neck.

To quantify these positioning variations, consider that a post-menopausal woman typically loses only approximately 1% of BMD per year and current osteoporosis treatment only increases BMD 0–2%. Hip positioning variations, however, are up to three times as large as BMD changes to be measured. This forces doctors and researchers to wait several months before being able to confidently notice a clear trend of BMD loss or gain from data scattered by positioning variations.

The magnitude of positioning variations also requires researchers to increase the number of patients studied to achieve statistically significant results. In all cases, the size of the positioning variations results in increased costs and delayed assessments.

In light of the foregoing, there is a need for a hip positioning apparatus which improves the precision of hip positioning to present the same femoral neck aspect for successive DXA scans. Such a hip positioning apparatus will reduce the errors caused by position variations and thus improve the accuracy of predicting hip fracture and accessing fracture treatment.

There is also a need for a hip positioning device that is lightweight, simple to install, easily adjusted to individual anatomical differences, and easy for the scanning technician to use.

Additional advantages of the invention will be set forth in the description which follows, and in part will be obvious from the description, or may be learned by practice of the invention. The advantages of the invention may be realized and obtained by means of the instrumentalities and combinations particularly pointed out in the appended claims.

SUMMARY OF THE INVENTION

Accordingly, the present invention is directed to a hip positioning apparatus that substantially obviates one or more of the problems due to limitations and disadvantages of the related art.

In accordance with the purposes of the invention as embodied and broadly described herein, the apparatus of this invention maintains an individual in an immobilized state for DXA scanning while abducting the individual's legs and adducting his feet.

More specifically, the apparatus for positioning the hips of an individual in an immobile position comprises a frame; a centering member mounted to the frame for engaging the groin of the individual; a pair of knee restraints mounted to the frame and spaced from the centering member and from each other to secure the knees of the individual in a manner to ensure that the knees are fully extended and the legs of the individual are spaced apart a predetermined amount; and a pair of foot restraints pivotally mounted to the frame and each aligned with a respective one of the knee restraints and the centering member to connect to a respective one of the feet of the individual thereby to hold the individual's groin against the centering member and immobilize the legs of the individual relative to the frame. Each of the foot restraints includes a clamping member, rotatably connected to the respective foot restraint, to hold the respective one of the individual's feet at a predetermined angle relative to the individual's body.

Both the foregoing general description and the following detailed description are exemplary and explanatory and are intended to provide further explanation of the invention as claimed.

The accompanying drawings which are incorporated in and constitute a part of the specification, illustrate an embodiment of the invention and together with the general description given above plus the detailed discussion which follows serve to explain the principles of the invention.

DESCRIPTION OF PREFERRED EMBODIMENTS

Reference will now be made in detail to the present preferred embodiments of the invention, examples of which are illustrated in the accompanying drawings.

The present invention allows repeatable measurements of BMD and BMC by immobilizing a patient's legs in a fully extended, abducted position, while holding the patient's feet in adducted position. The present invention allows a patient to be immobilized by providing a frame on which a patient is placed, a centering member, a pair of knee restraints to secure the knees in a fully extended and abducted position, and a pair of foot restraints to secure the patient's feet in an adducted position.

Figure 1:
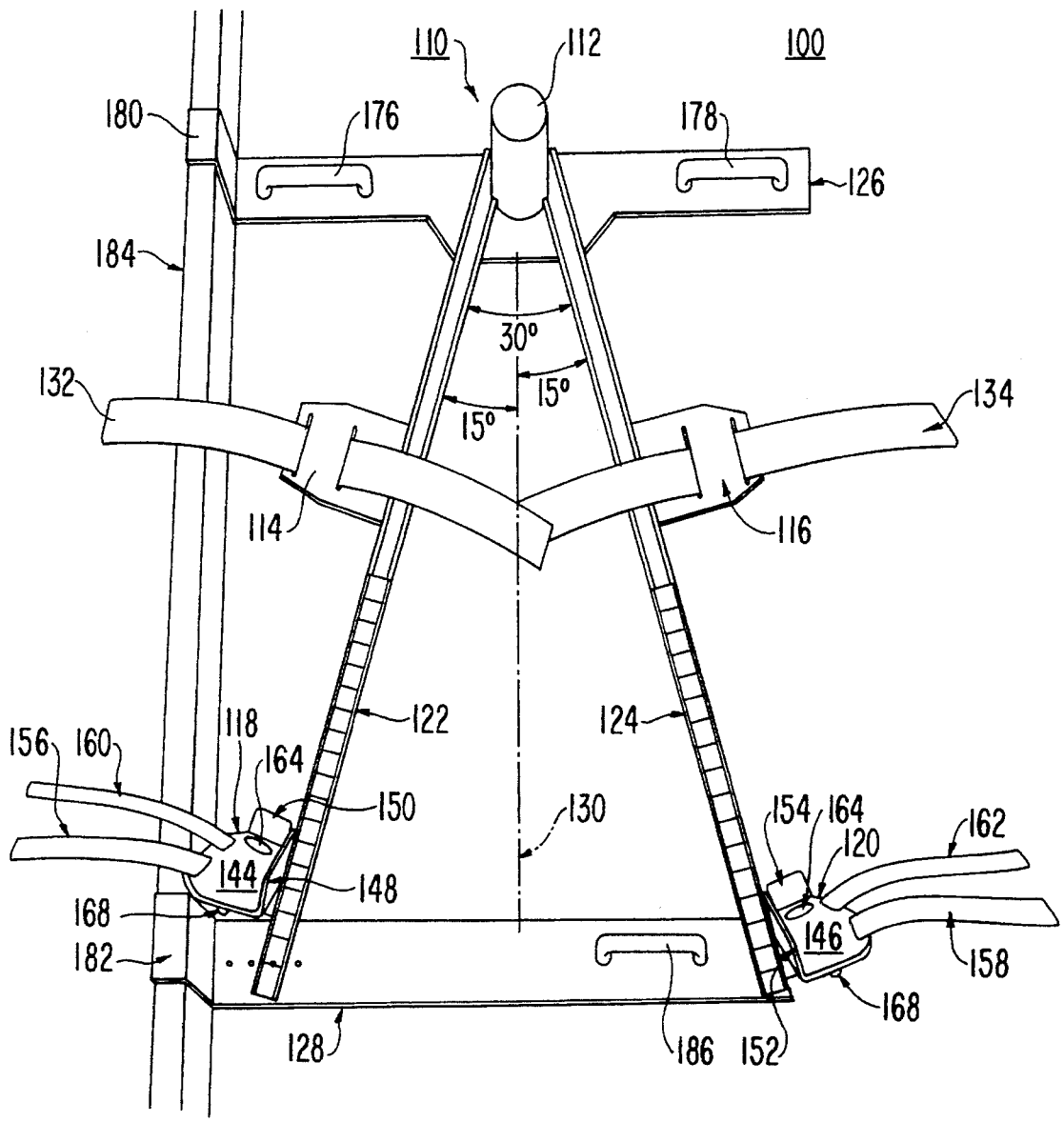
FIG. 1 is an illustration of a hip positioning apparatus in accordance with a first preferred embodiment of the invention.

The preferred embodiment 100 of the invention shown in FIG. 1 includes a frame 110, a centering member 112 mounted to frame 110, a pair of knee restraints 114 and 116 mounted to frame 110, and a pair of foot restraints 118 and 120 pivotally mounted to frame 110.

Frame 110 includes leg guides 122 and 124 attached to upper tie plate 126 at centering member 112 and lower tie plate 128 such that the leg guides 122 and 124 form a triangle with lower tie plate 128 as a base Preferably, the triangle has an angle of 30 degrees at centering member 112 so that each of leg guides 122 and 124 extends 15 degrees from a midline as illustrated in FIG. 1.

Leg guides 122 and 124 provide mounting locations for knee restraints 114 and 116 and foot restraints 118 and 120, respectively. Knee restraints 114 and 116 include knee restraint straps 132 and 134, respectively, each threaded through two slits to immobilize a patient's knee in a fully extended position, while abducting each of the patient's legs 15 degrees from the midline.

Leg guides 122 and 124 also provide support for foot restraints 118 and 120 to immobilize a patient's feet at an angle relative to a median axis running through the center of the patient.

Figure 2:
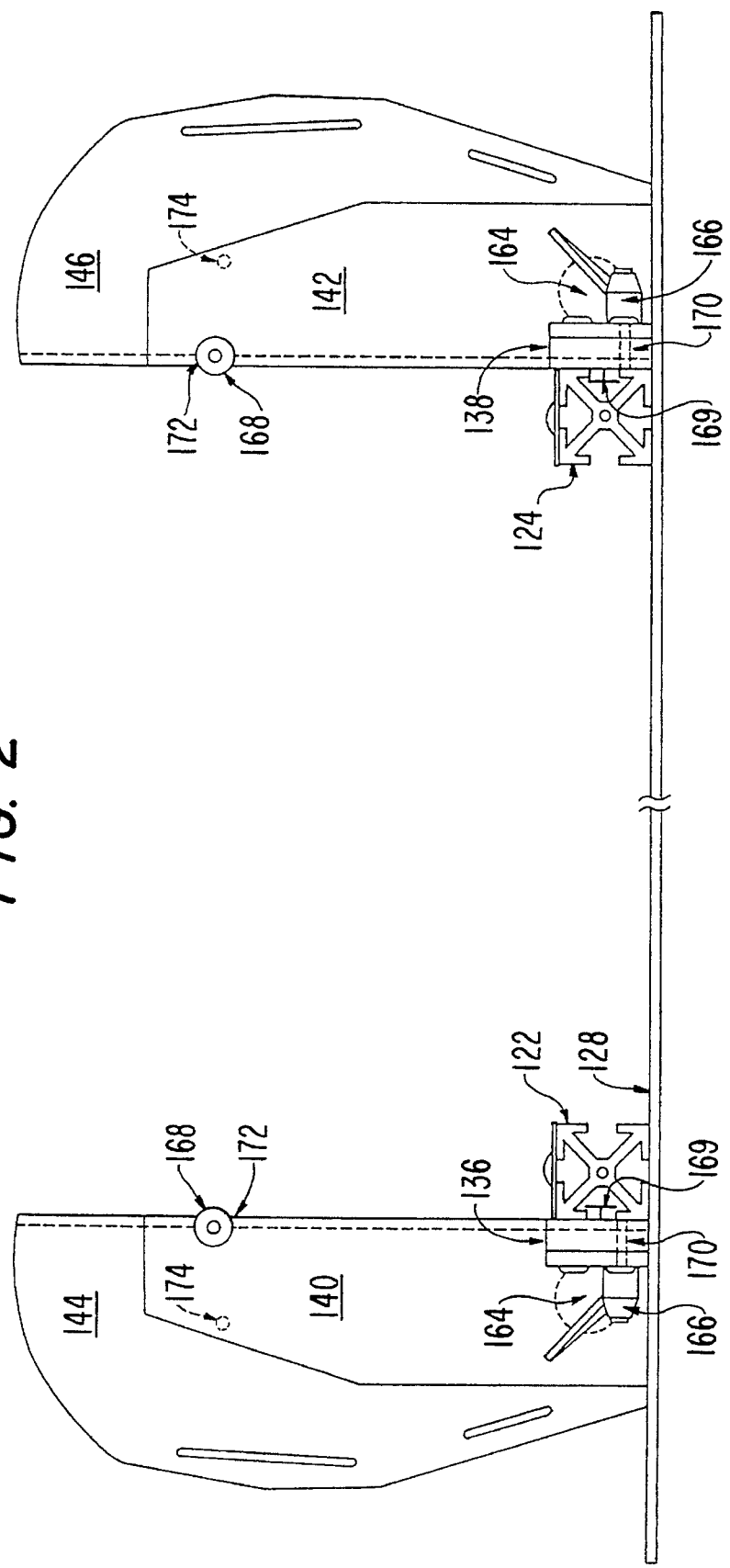
FIG. 2 is an end view of a preferred embodiment of the invention in a 0 degree adducted position.

Foot restraints 118 and 120, which are also shown in FIG. 2, include connectors 136 and 138; fixed plates 140 and 142; rotatable plates 144 and 146; heel pivots 164; extensions 148, 150, 152, and 154; metatarsal straps 156 and 158; ankle straps 160 and 162; and locking mechanisms 168. FIG. 2 illustrates foot restraints 118 and 120 viewed toward upper tie plate 126.

As FIGS. 1 and 2 illustrate, foot restraints 118 and 120 are slidably attached to leg guides 122 and 124 by connectors 136 and 138 including screw assemblies 166. Connectors 136 and 138 include T-shaped protrusions 169 which hold connectors 136 and 138 against leg guides 122 and 124 allowing connectors 136 and 138 to move along leg guides 122 and 124. When an operator chooses to fix either foot restraint 118 or 120 in a particular location along its respective leg guide, he turns respective screw assembly 166 in a clockwise direction forcing screw 170 against respective leg guide 122 or 124 preventing further sliding along leg guides 122 and 124, respectively. Screw assemblies 166 are released by rotating them in a counterclockwise direction.

Fixed plates 140 and 142 are attached to connectors 136 and 138 to provide bilateral 10 degrees plantar deflection to the plane in which leg guides 122 and 124 lie. Rotatable plates 144 and 146 are attached to fixed plates 140 and 142, respectively, via pivots 164 allowing rotatable plates 144 and 146 to rotate toward the midline. FIG. 2 illustrates rotatable plates 144 and 146 with no rotation about pivots 164.

Figure 3:
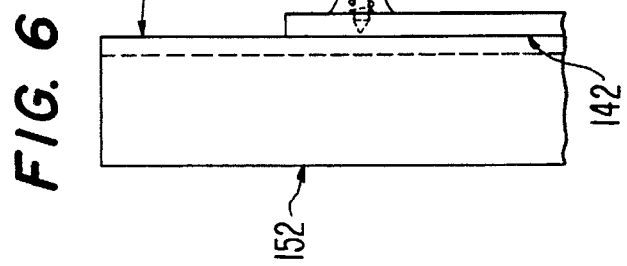
FIG. 3 is a side view of an upper portion of a foot restraint of the preferred embodiment of FIG. 1 for a patient's right foot locked in an upright position.
Figure 4:
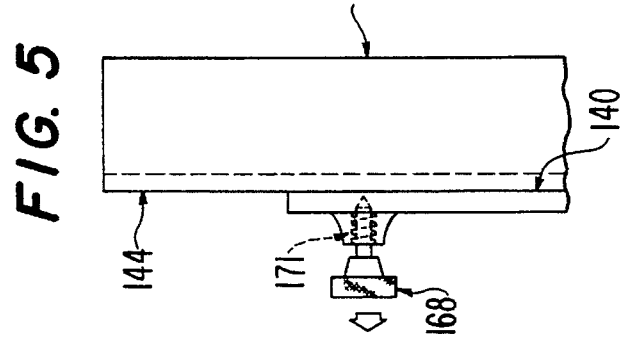
FIG. 4 is a side view of an upper portion of a foot restraint of the preferred embodiment of FIG. 1 for the left foot locked in an upright position.

As shown in FIGS. 3 and 4, which illustrate side views of an upper portion of foot restraints 118 and 120, respectively, locking mechanisms 168, including springs 171, are spring-held protrusions which, in an at-rest state, extend through fixed plates 140 and 142 and against rotatable plates 144 and 146.

Figure 5:
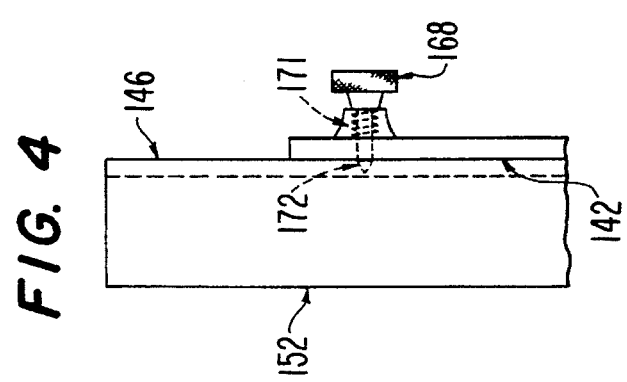
FIG. 5 is a side view of an upper portion of the foot restraint of FIG. 3 in an unlocked state.
Figure 6:
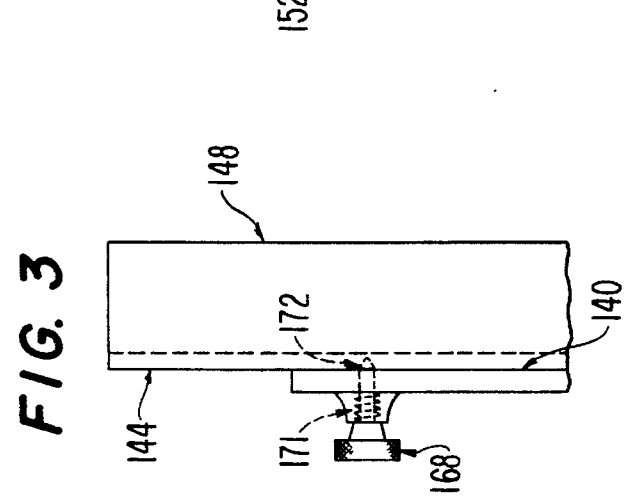
FIG. 6 is a side view of an upper portion of the foot restraint of FIG. 4 in an unlocked state.

As illustrated in FIGS. 1, 5, and 6, FIGS. 5 and 6 illustrating the same view as FIGS. 3 and 4, respectively, rotatable plates 144 and 146 have holes 172 into which locking mechanisms 168 slide, locking rotatable plates 144 and 146 in a non-rotated position.

Figure 7:
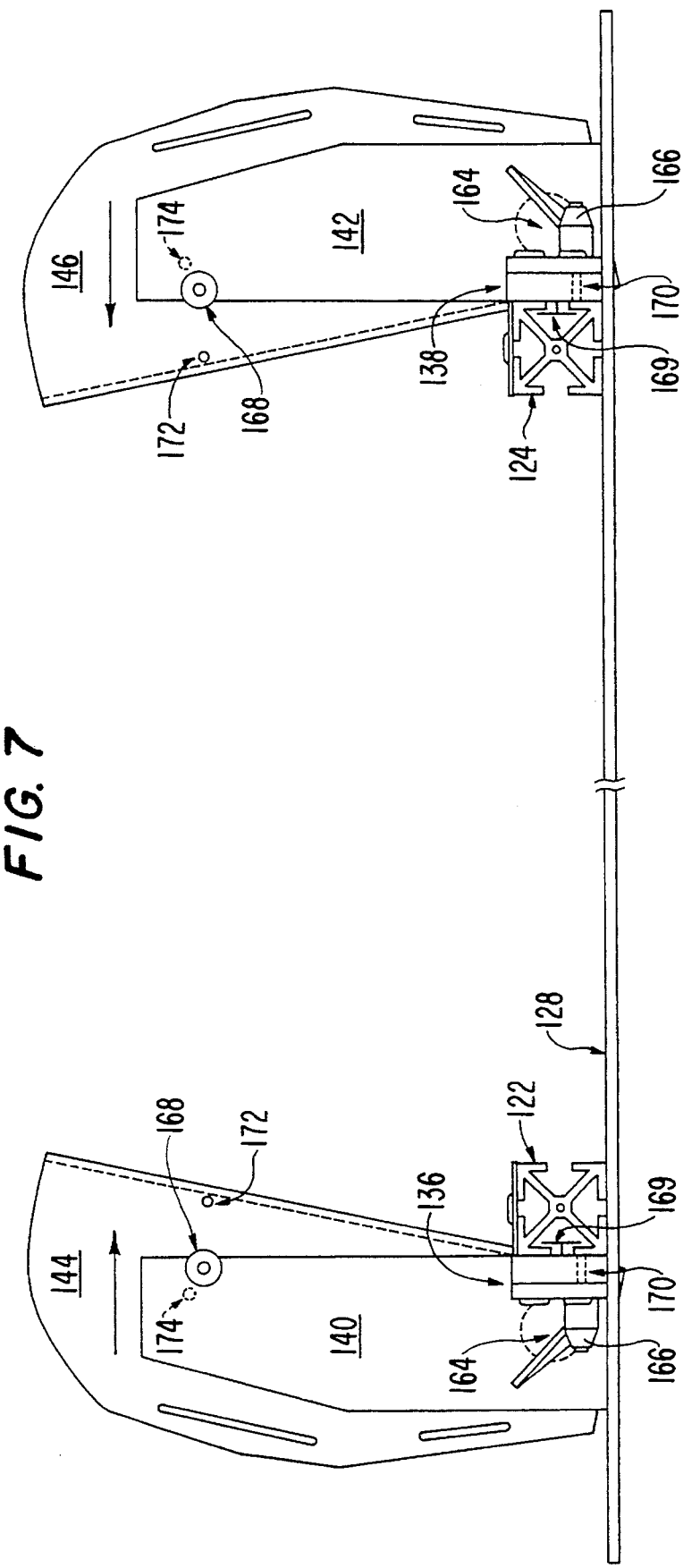
FIG. 7 is an end view of a preferred embodiment of the invention with foot restraints locked in a 15 degree adducted position.

Pivots 164 allow rotatable plates 144 and 146 to be rotated in the direction of the midline as illustrated in FIG. 7. Holes 174 are located in a position allowing rotatable plates 144 and 146 to be locked 15 degrees rotated toward the midline.

Rotatable plates 144 and 146 include foot extensions 148 and 152, perpendicular to rotatable plates 144 and 146, attached at the edges near pivots 164 connected to connectors 136 and 138. Rotatable plates 144 and 146 also include extensions 150 and 154, also perpendicular to rotatable plates 144 and 146, attached near the edges near pivots 164. Ankle straps 160 and 162 are attached to rotatable plates 144 and 146 near the edges opposite the edges connected to extensions 148 and 152. Ankle straps 160 and 162 allow a clinician to fix the patient's ankle against rotatable plates 144 and 146, extensions 150 and 154 as well as extensions 148 and 152. Metatarsal straps 156 and 158, also attached to rotatable plates 144 and 146 near the edges opposite the edges connected to extensions 148 and 152, allow the operator to fix the upper portion of the patient's feet against rotatable plates 144 and 146 and extensions 148 and 152.

In use, a patient's feet are positioned against rotatable plates 144 and 146 so that the patient's heels are placed against extensions 150 and 154 and the inside of the patient's feet are placed against extensions 148 and 152. Ankle straps 160 and 162 secure the patient's heels against extensions 150 and 154 and rotatable plates 144 and 146, and metatarsal straps 156 and 158 secure the patient's feet against extensions 148 and 152 and rotatable plates 144 and 146.

Rotatable plates 144 and 146 may then be freed by pulling locking mechanisms 168, allowing rotatable plates 144 and 146 to rotate about pivots 164 in the directions shown in FIG. 7. When rotatable plates 144 and 146 are rotated 15 degrees relative to fixed plates 140 and 142, as shown in FIG. 7, rotatable plates 144 and 146 are locked into position by allowing locking mechanisms 168 to slip into holes 174 located at 15 degrees of rotation from holes 172.

Frame 110 also provides support for hand-holds 176 and 178, respectively, and mounting brackets 180 and 182. Hand-holds 176 and 178 are attached on opposite ends of upper tie plate 126. Mounting bracket 180, attached to one end of upper tie plate 126, and mounting bracket 182, attached to one end of lower tie plate 128, provide slidable attachment to scanning table arm guard 184. Lower tie plate 128 also provides support for hand-hold 186.

With this understanding of the preferred embodiment of the hip positioning apparatus, its operation will be described.

Before scanning a patient's hips, apparatus 100 is placed on a scanning table (not shown) below an x-ray source (not shown). The sliding mounting brackets 180 and 182 in FIG. 1 should be placed over scanning table arm guard 184 to center frame 110 on the scanning table. Lower tie plate 128 is at the end of the table where a patient's feet will lie.

The patient then lies down on the scanning table and, using hand-holds 176 and 178, pulls herself into a position with her groin against centering member 112. The patient fully extends her knees which are strapped in position using knee restraint straps 132 and 134 of knee restraints 114 and 116. Frame 110's design assures that both of the patient's legs are fully extended at the hips and knees, while being held in 15 degrees of abduction at both hip joints. This abducted position for both hips is unique to scanning procedures commonly used for measuring hip BMD and BMC. By abducting both hips on the frame 110 to 15 degrees from the midline, projections of the femoral neck usually allow bone density analyses without overlapping projections of adjacent hip anatomy, as with present equipment.

Next, foot restraints 118 and 120 are freed and slid against the bottom of the patient's feet and fixed by tightening screw assemblies 166. The patient's feet should fit snugly against rotatable plates 144 and 146. Straps 156, 160, 158, and 162 then secure the patient's feet against rotatable plates 144 and 146, extensions 148, 150, 152 and 154. Locking mechanisms 168 are then pulled releasing rotatable plates 144 and 146 which are rotated inward on pivots 164 into the 15 degree adducted position as locking mechanisms 168 slide into holes 174.

By securing and immobilizing the knees, feet, and ankles, and establishing a countertension between the feet and the hips in equal positions of abduction, the patient positioning of this invention assures that all of the internal rotation occurs at the hip joint. Isolating rotation to the hip joint greatly increases BMD and BMC reproducibility.

The clinician then sights along the midline to centering member 112 to assure alignment of the patient's torso and head with the midline. When this alignment is complete, the patient is ready for scanning of the hips.

Figure 8:
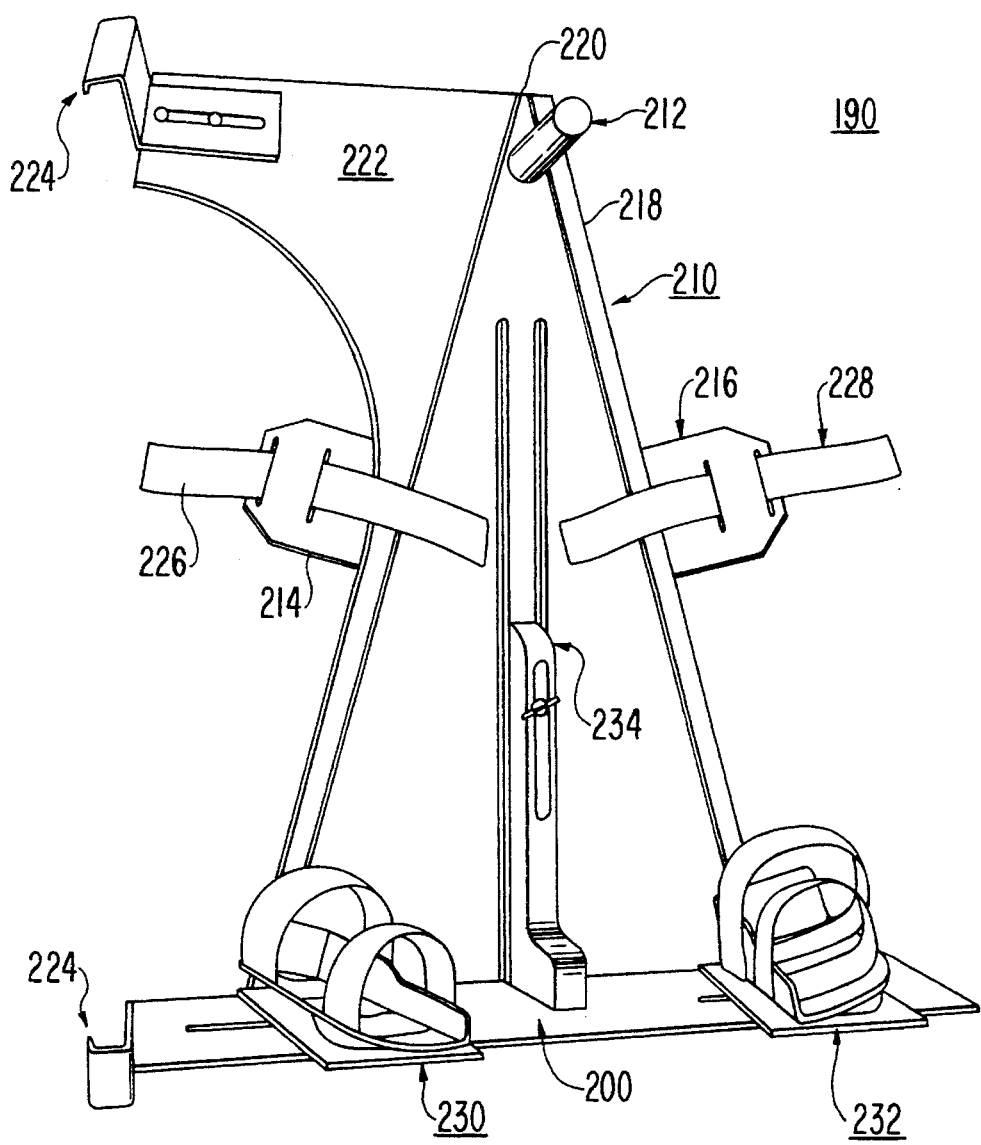
FIG. 8 is an illustration of a hip positioning apparatus according to a second embodiment of the invention.
Figure 9:
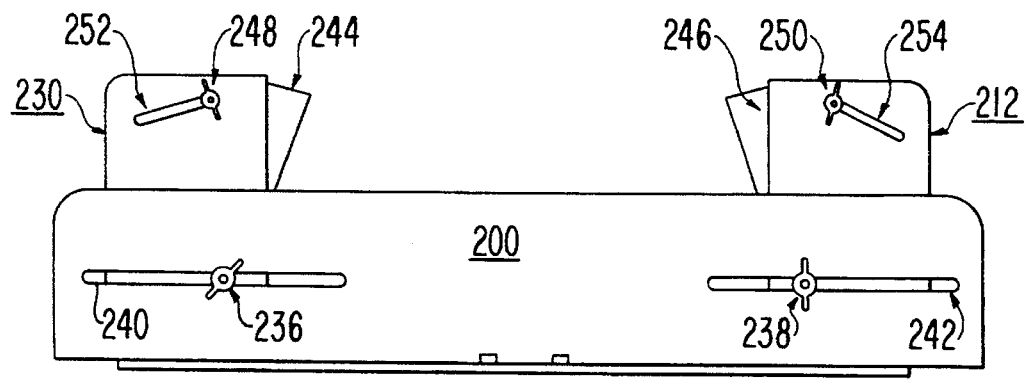
FIG. 9 is an end view of a foot carrier of the hip positioning apparatus of FIG. 8.

FIGS. 8 and 9 show another embodiment of a positioning device which accomplishes the same result as described previously. The primary difference between this embodiment and that described by FIG. 1 lies in the use of a single structure foot carrier 200, which mounts foot restraints 230 and 232 that can be moved toward or away from a centerline to provide a 15 degree abduction of each leg. The entire foot carrier 200 can be moved toward or away from the patient to accommodate varying patient heights. The 15 degree adduction of the feet is accomplished using wing-nut assemblies 248 and 250 to lock rotatable plates 244 and 246 in 0 or 15 degree adducted positions. A pivot (not shown) permits rotation of the foot restraint to a 15 degree adducted position.

To operate this system, a clinician sets foot carrier 200 to match the patient's leg length, then slides and fixes foot restraints 230 and 232 laterally to achieve 15 degrees of abduction of the patient's legs. Finally the clinician rotates rotatable plates 244 and 246 to achieve a 15 degree adduction of the patient's feet.

Specifically, the hip positioning apparatus 190 illustrated in FIGS. 8 and 9 includes support frame 210, centering member 212 knee restraints 214 and 216, and foot carrier 200.

Support frame 210 includes an isosceles triangle portion 218 whose sides form a triangle with an included angle of 30 degrees at reference point 220 as shown in FIG. 8. Support frame 210 also includes an attachment portion 222 which provides support for mounting brackets 224. Mounting brackets 224 provide for slidable attachment to a scanning table arm guard (not shown).

Centering member 212 is located below the vertex of the 30 degree angle as illustrated in FIG. 8. Along the equal sides of the triangle are knee restraints 214 and 216, including straps 226 and 228, respectively, for securing the patient's knees in a fully extended position.

Foot carrier 200 provides a 10° plantar deflection and support for foot restraints 230 and 232, is slidably attached to support frame 210 via guide track 234 which, in the preferred embodiment bisects the 30 degree angle of frame 210. Foot restraints 230 and 232 are attached to foot carrier 200 by wing-nut assemblies 236 and 238 which allow lateral movement in restraint tracks 240 and 242. After a patient lies on support frame 210, the operator slides foot carrier 200 against the bottom of the patient's feet. The patient's feet are placed in foot restraints 230 and 232 in a similar fashion as described in reference to foot restraints 118 and 120 of FIG. 1.

Next, foot restraints 230 and 232 slide within restraints tracks 240 and 242 to position the patient's legs in a 15 degree abducted position. Wing-nut assemblies 236 and 238 are tightened to fix the foot restraint's position. Rotatable plates 244 and 246 are then rotated by sliding wing-nut assemblies 248 and 250 in rotating tracks 252 and 254 to achieve a 15 degree adducted position of the foot and ankle.

The improvements provided by this invention in hip placement and scanning accuracy will allow researchers and doctors to detect the effectiveness of osteoporosis treatment and assessment of skeletal abnormalities more quickly and positively than with conventional devices. These improvements will also allow the researcher to achieve a statistically significant result with far fewer patients.

Scan accuracy is improved by reducing the error caused by position variations. The hip BMD and BMC values from patients positioned with this invention are much more reproducible than they are with technology currently in use.

Independent clinical evaluations have shown positioning variations of 0.2–1.1% for this invention, four to five times less than results achieved by existing technology.

Additional advantages and modifications will readily occur to those skilled in the art from reading the description of the preferred implementations and from understanding the concepts of this invention. The invention in its broader aspects is not limited to the specific details, representative apparatus, and illustrative examples shown and described above. Departures may be made from such details without: departing from the spirit or scope of the general inventive concept as defined by the appended claims and their equivalents.

What is claimed is:

1. An apparatus for positioning the hips of an individual in an immobile position comprising:

a frame including a pair of leg guides;

a centering member mounted to the frame for engaging the groin of the individual, said centering member lying between said pair of leg guides along a median axis;

a pair of knee restraints mounted to the frame and spaced from the centering member and from each other to secure the knees of the individual in a manner to ensure that the knees are fully extended and the legs of the individual are pivoted away from the median axis; and a pair of foot restraints pivotally mounted to the frame and each aligned with a respective one of the knee restraints and the centering member to connect to a respective one of the feet of the individual thereby to hold the individual's groin against the centering member and immobilize the legs of the individual relative to the frame, each of the foot restraints including a clamping member, rotatably connected to the respective foot restraint, to hold the respective one of the individual's feet, said clamping member being rotatable so as to pivot the foot with respect to the respective leg guide toward the median axis.

2. An apparatus according to claim 1, wherein the frame and the knee restraints pivot the individual's legs apart and away from the median to axis define an angle between the legs of approximately 30 degrees.

3. An apparatus according to claim 1, wherein the clamping member rotates to pivot the individual's foot with respect to the leg guide approximately 15 degrees toward the median axis.

4. An apparatus according to claim 1, wherein each foot restraint includes a foot support connector slidably attached to the frame;

a sole support plate attached to the foot support connector; and wherein the clamping means includes a rotatable support member rotatably attached to the sole support plate.

5. An apparatus according to claim 4, wherein each clamping means also includes foot extensions perpendicularly attached to the rotatable support member for holding the individual's foot.

6. An apparatus according to claim 4, wherein each clamping means further includes foot restraint straps attached to the rotatable support member for restraining the individual's foot; and a foot locking mechanism attached to the sole support plate and the rotatable support member for locking the rotatable support member in a plurality of predetermined rotated angles relative to the sole support plate.

7. The apparatus of claim 1 further including slidable support means, coupled to the frame, for connecting the frame to another structure.

8. An apparatus for positioning the hips of an individual in an immobile position comprising:

an upper tie plate;

a centering member, attached to the upper tie plate, for engaging the groin of the individual, said centering member lying along a median axis between said pair of leg guides;

left leg and right leg support members, attached to the centering member to define an angle therebetween, to provide restraining support, respectively, for the individual's left and right legs;

a lower tie plate attached to the left and right support members distal from the attachment of the left and right support members to the centering member, such that the left and right leg support members form a triangle with the lower tie plate as a base;

left and right knee restraints, mounted to the left and right leg support members, respectively, and spaced from said centering member to secure the knees of the individual in a manner to ensure that the knees are fully extended and the legs of the individual are pivoted away from the median axis; and left and right foot restraints pivotally and slidably mounted to the left and right leg support members, respectively, each of the foot restraints having a foot strap to provide support for the individual's left and right feet, respectively, and thereby to hold the individual's groin against the centering member and immobilize the legs of the individual relative to the frame, each foot restraint being rotatable to pivot each foot with respect to the respective leg support member towards the median axis.

9. The apparatus of claim 8 wherein each of the foot restraints includes a clamping member, rotatably connected to the respective foot restraint, to hold the respective one of the individual's feet at a predetermined angle relative to the individual's body.

10. A hip positioning apparatus according to claim 5, wherein the left leg and right leg support members and knee restraints pivot the legs away from the median axis to define an angle between the legs of about 30 degrees.

11. A hip positioning apparatus according to claim 8 further including left and right individual grasping members attached to the upper tie plate to provide left hand and right hand grasping points for the individual.

12. A hip positioning apparatus according to claim 9, wherein each of the foot restraints includes a foot support connector slidably attached to the frame;

a sole support plate attached to the foot support connector; and wherein the clamping means includes a rotatable support member rotatably attached to the sole support plate.

13. An apparatus according to claim 9, wherein each clamping means also includes foot extensions perpendicularly attached to the rotatable support member for holding the individual's foot.

14. An apparatus according to claim 9, wherein each clamping means further includes foot restraint straps attached to the rotatable support member for restraining the individual's foot; and a foot locking mechanism attached to the sole support plate and the rotatable support member for locking the rotatable support member in a plurality of predetermined rotated angles relative to the sole support plate.

* * * * *